US009546947B2

(12) United States Patent
Kobayashi et al.

(10) Patent No.: US 9,546,947 B2
(45) Date of Patent: Jan. 17, 2017

(54) IMAGING SYSTEM (71) Applicant: FUJIFILM Corporation, Tokyo (JP)

(72) Inventors: Takashi Kobayashi, Ashigarakami-gun (JP); Yasunori Ohta, Ashigarakami-gun (JP); Yasutake Tanaka, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/947,058

(22) Filed: Nov. 20, 2015

(65) Prior Publication Data

US 2016/0153889 A1    Jun. 2, 2016

(30) Foreign Application Priority Data

Nov. 28, 2014  (JP) ................................. 2014-241018

(51) Int. Cl.
*G01N 21/01*  (2006.01)
*G01N 21/64*  (2006.01)
(Continued)

(52) U.S. Cl.
CPC .......... *G01N 21/01* (2013.01); *G01N 21/6428* (2013.01); *G01N 21/6456* (2013.01); (Continued)

(58) Field of Classification Search
None
See application file for complete search history.

(56) References Cited

U.S. PATENT DOCUMENTS

2003/0036860 A1* 2/2003 Rice .......................... G01J 1/08
                                                        702/57
2005/0051723 A1* 3/2005 Neagle .................... C12M 41/14
                                                        250/306
(Continued)

FOREIGN PATENT DOCUMENTS

EP          2857842 A1    4/2015
JP       2004-021554 A    1/2004
(Continued)

OTHER PUBLICATIONS

Extended European Search Report for European Application No. 15194241.4, dated Mar. 16, 2016.

*Primary Examiner* — Shahbaz Nazrul
(74) *Attorney, Agent, or Firm* — Birch, Stewart, Kolasch & Birch, LLP (57) ABSTRACT

Disclosed is an imaging system which includes an imaging device to be used by multiple users, allows each user to perform imaging at an appropriate timing, and is capable of efficiently using the imaging device. An imaging system includes an imaging device, a plurality of terminal devices, and an authorization unit which gives the terminal devices the authority to specify controllable functions of the imaging device. The authorization unit switches between a first state where the terminal devices are given a first authority to exclusively occupy a part of functions of the imaging device with a controllable state and a second state where one terminal device is given a second authority to exclusively occupy and control the part of functions and to release the occupation, and the terminal devices other than one terminal device are given a third authority with the restriction of the control of the part of functions.

20 Claims, 10 Drawing Sheets (51) Int. Cl.
*G01N 35/00* (2006.01)
*G01N 21/76* (2006.01)
*G01J 3/44* (2006.01)

(52) U.S. Cl.
CPC ....... *G01N 21/76* (2013.01); *G01N 35/00871* (2013.01); *G01J 3/44* (2013.01); *G01N 2021/0131* (2013.01); *G01N 2021/0175* (2013.01); *G01N 2021/0181* (2013.01); *G01N 2021/6439* (2013.01)

(56) References Cited

U.S. PATENT DOCUMENTS

| | | | | |
|---|---|---|---|---|
| 2008/0103390 | A1* | 5/2008 | Contag | G01N 21/6428 600/427 |
| 2010/0169423 | A1* | 7/2010 | Eguchi | A61B 6/4233 709/204 |
| 2010/0315502 | A1* | 12/2010 | Tafas | G02B 21/365 348/79 |
| 2012/0235016 | A1 | 9/2012 | Weiner et al. | |
| 2015/0125961 | A1* | 5/2015 | Goemann-Thoss | G01N 35/00871 436/43 |

FOREIGN PATENT DOCUMENTS

| | | |
|---|---|---|
| JP | 2008-268048 A | 11/2008 |
| JP | 2009-199194 A | 9/2009 |
| JP | 2013-165328 A | 8/2013 |
| JP | 2014-010136 A | 1/2014 |

* cited by examiner

IMAGING SYSTEM

CROSS-REFERENCE TO RELATED APPLICATIONS

The present application claims priority under 35 U.S.C. §119 to Japanese Patent Application No. 2014-241018, filed on Nov. 28, 2014. Each of the above application(s) is hereby expressly incorporated by reference, in its entirety, into the present application.

BACKGROUND OF THE INVENTION

1. Field of the Invention

The present invention relates to an imaging system including an imaging device which photoelectrically reads fluorescence or chemiluminescence emitted from an object to image the object, and a plurality of terminal devices which output control information for controlling the imaging device to the imaging device.

2. Description of the Related Art

Hitherto, imaging devices in which an object is arranged in a housing and irradiates the object with light using a light source provided in the housing to image the object have been used in various fields. Among such imaging devices, an imaging device which selectively uses an imaging method primarily according to the type of object, and images chemiluminescence, fluorescence, or reflected light from an object, or transmitted light transmitted through the object by an imaging element to generate an image has been disclosed.

Since such an imaging device is expensive, in many cases, such an imaging device is thus installed as common equipment in a research facility, and is shared and used by multiple users. For example, JP2014-010136A discloses a system in which an imaging device is used by multiple users, and suggests that, when there are use requests for the imaging device from multiple users, imaging processing or image analysis processing is performed according to the use request of each user according to a priority set in advance.

SUMMARY OF THE INVENTION

It is necessary to image a sample to be imaged as soon as possible after creation and to reliably image the sample at an appropriate timing. However, according to the method described in JP2014-010136A, since the priority set in advance does not necessarily take the creation time of the sample into consideration, the user may not perform imaging at an appropriate timing.

A method in which each user plans the creation time of the sample, reserves the use time of the imaging device in advance, and uses the imaging device according to the reserved time is considered.

However, the creation of the sample may not be performed as planned. Since a user plans this case and reserves a somewhat long use time, this is considered to deteriorate the use efficiency of the imaging device. In particular, when imaging chemiluminescence or fluorescence, or the like, since chemiluminescence or fluorescence emitted from an object is feeble, the imaging time (exposure time) may be extended.

JP2004-021554A discloses that, when multiple users uses one multi-function machine, the access level of each user is restricted; however, when multiple users use the imaging device described above, each user cannot perform imaging at an appropriate timing, and there is no disclosure of a method which efficiently uses the imaging device.

JP2013-165328A discloses that, in a multi-function machine accessible from multiple users, a function setting item which is set by a predetermined user cannot be set by other users; however, when multiple users use the imaging device described above, each user cannot perform imaging at an appropriate timing, and there is no disclosure of a method which efficiently uses the imaging device.

An object of the invention is to provide an imaging system which includes an imaging device to be used by multiple users and is capable of allowing each user to perform imaging at an appropriate timing and efficiently using the imaging device, in consideration of the problems described above.

An imaging system of the invention includes an imaging device which photoelectrically reads fluorescence or chemiluminescence emitted from an object to image the object, a plurality of terminal devices which output control information for controlling the imaging device to the imaging device, and an authorization unit which gives the respective terminal devices an authority to specify controllable functions of the imaging device. The authorization unit switches between a first state where the respective terminal devices are given a first authority to exclusively occupy a part of functions of the imaging device and to bring the part of functions into a controllable state and a second state where one terminal device among the plurality of terminal devices is given a second authority to exclusively occupy and control the part of functions and to release the occupation, and the terminal devices other than one terminal device are given a third authority with the restriction of the control of the part of functions.

In the imaging system of the invention, the first authority may include an authority capable of receiving a first instruction operation to exclusively occupy a part of functions of the imaging device and to bring the part of functions into a controllable state, and the authorization unit may switch from the first state to the second state when receiving the first instruction operation.

It is preferable that the third authority does not include an authority capable of receiving the first instruction operation.

The second authority may include an authority capable of receiving a second instruction operation to release the occupation of the part of functions, and the authorization unit may switch from the second state to the first state when receiving the second instruction operation.

The part of functions may be a function of imaging.

The authorization unit may give a specific terminal device other than terminal devices given the second authority a fourth authority including an authority to release the occupation of the part of functions by the terminal device given the second authority in the second state.

The fourth authority may include an authority capable of receiving a third instruction operation to release the occupation of the part of functions, and the authorization unit may switch from the second state to the first state when receiving the third instruction operation.

The authorization unit may give the specific terminal device a fifth authority in the first state, and the fifth authority may include an authority to give the terminal devices other than the specific terminal device a sixth authority with the restriction of controllable functions further than the third authority.

The fifth authority may include an authority capable of receiving a fourth instruction operation to give the terminal devices other than the specific terminal device the sixth authority, and the authorization unit may switch to a third state where the terminal devices other than the specific terminal device are given the sixth authority when receiving the fourth instruction operation in the first state.

The authorization unit may give the specific terminal device a seventh authority in the third state, and the seventh authority may include an authority to release the restriction of the controllable functions in the terminal devices other than the specific terminal device.

The fifth authority may include an authority capable of receiving a fifth instruction operation to release the restriction of the controllable functions in the terminal devices other than the specific terminal device, and the authorization unit may give the terminal devices other than the specific terminal device the first authority when receiving the fifth instruction operation in the third state.

The fifth authority may include an authority to prohibit the control of the imaging device by the terminal devices other than the specific terminal device.

The fourth instruction operation may be an instruction operation to prohibit the control of the imaging device by the terminal devices other than the specific terminal device.

The fifth instruction operation may be an instruction operation to release the prohibition of the control of the imaging device by the terminal devices other than the specific terminal device.

According to the imaging system of the invention, the authorization unit which gives the respective terminal devices an authority to specify the controllable functions of the imaging device is provided. The authorization unit sets the first state where the respective terminal devices are given a first authority to exclusively occupy a part of functions of the imaging device and to bring the part of functions into a controllable state, and switches to the second state where one terminal device among the plurality of terminal devices is given a second authority to exclusively occupy and control the part of functions and to release the occupation, and the terminal devices other than one terminal device are given a third authority with the restriction of the control of the part of functions.

The authority given to each terminal device is switched from the first state to the second state, whereby the users of the terminal devices given the second authority can execute the part of functions at an appropriate timing without being affected or obstructed by other terminal devices. That is, the imaging function can be executed at an appropriate timing.

In the terminal devices given the second authority, when the occupation state of the part of functions is released, the authority given to each terminal device can be returned from the second state to the first state; therefore, the users of other terminal devices can exclusively occupy and control the part of functions quickly, and as a result, the use efficiency of the imaging device can be improved.

DESCRIPTION OF THE PREFERRED EMBODIMENTS

Figure 1:
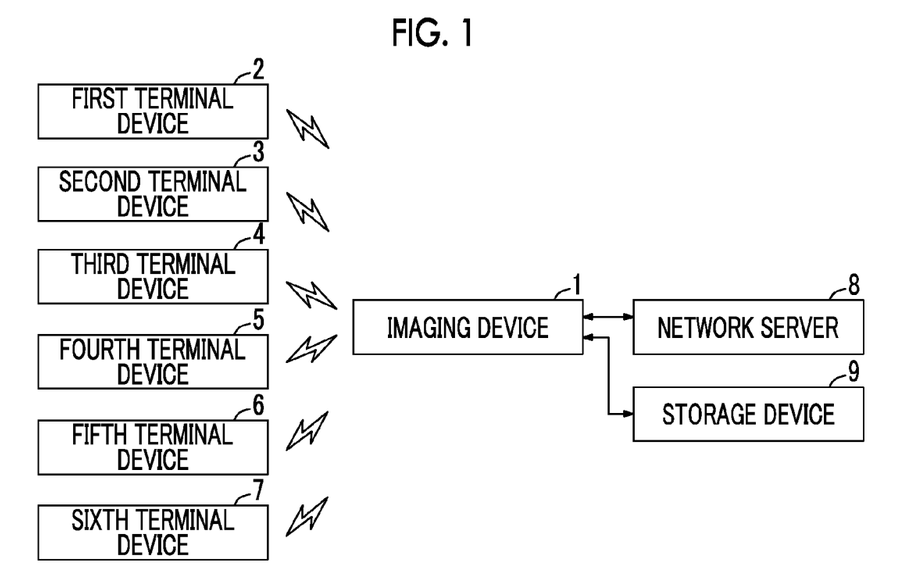
FIG. 1 is a block diagram showing the schematic configuration of an imaging system using an embodiment of an imaging device of the invention.
Figure 2:
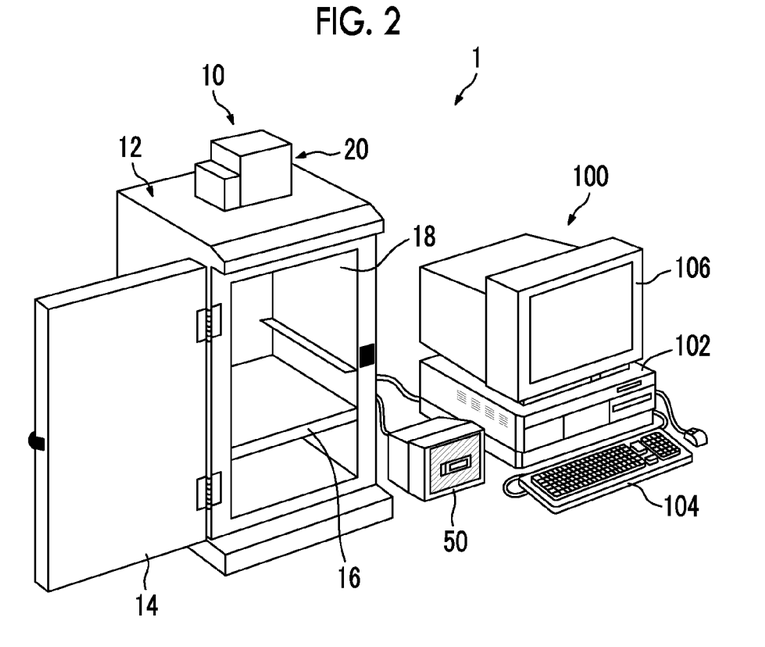
FIG. 2 is a schematic perspective view of the imaging device in the imaging system shown in FIG. 1.
Figure 3:
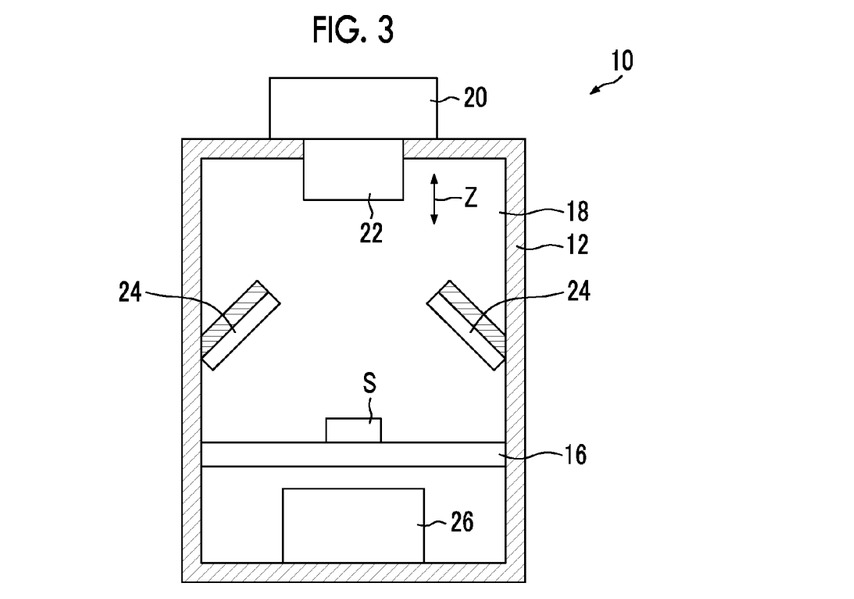
FIG. 3 is a schematic sectional view showing the internal configuration of the imaging device in the imaging system shown in FIG. 1.
Figure 4:
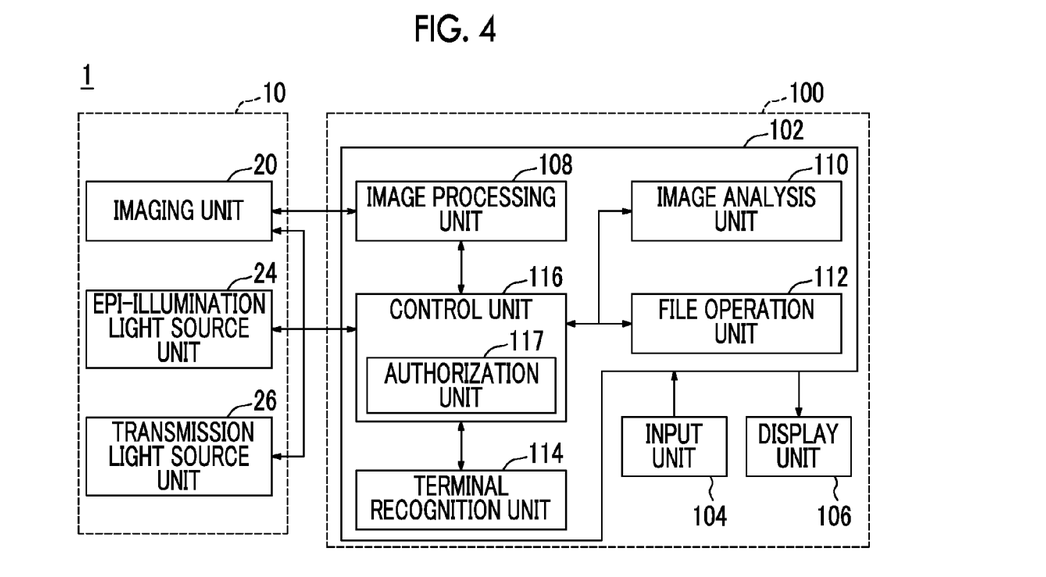
FIG. 4 is a block diagram showing the schematic configuration of the imaging device in the imaging system shown in FIG. 1.

Hereinafter, an imaging system which uses an embodiment of an imaging device and method of the invention will be described in detail referring to the drawings. FIG. 1 is a block diagram showing the schematic configuration of the imaging system of this embodiment, and FIG. 2 is a perspective view showing the schematic configuration of the imaging device in the imaging system shown in FIG. 1. FIG. 3 is a sectional view showing the internal configuration of an imaging device body shown in FIG. 2, and FIG. 4 is a block diagram showing the schematic configuration of the imaging device shown in FIG. 2.

As shown in FIG. 1, the imaging system of this embodiment includes an imaging device 1, first to sixth terminal devices 2 to 7, a network server 8, and a storage device 9.

The imaging device 1 photoelectrically reads fluorescence or chemiluminescence emitted from an object placed in the imaging device 1 to image the object, and the first to sixth terminal devices 2 to 7 output control information to the imaging device 1 and control the imaging function of the imaging device 1. The imaging device 1 of this embodiment operates based on the control information output from the first to sixth terminal devices 2 to 7, that is, is shared and used by multiple users.

The network server 8 and the storage device 9 temporarily store an electronic file (hereinafter, simply referred to as a file) including an image captured by the imaging device 1.

First, the imaging device 1 will be described in detail. As shown in FIGS. 2 and 3, the imaging device 1 includes an imaging device body 10 and an imaging control device 100.

The imaging device body 10 includes a housing 12 having a door 14, a stage 16 on which an object S is placed, an imaging unit 20, a lens unit 22, an epi-illumination light source unit 24, a transmission light source unit 26, and an object observation monitor 50.

The housing 12 has a hollow portion 18 formed in a substantially rectangular parallelepiped, and constitutes a black box where external light does not enter the hollow portion 18. The stage 16 on which the object S is placed is provided inside the housing 12. The door 14 shown in FIG. 2 is provided openably in the housing 12, and a user opens the door 14, places the object S on the stage 16, and then closes the door 14, thereby storing the object S in the housing 12. The stage 16 is formed of a material which transmits light from the transmission light source unit 26.

The imaging unit 20 is fixed to the top surface of the housing 12, includes, for example, an imaging element, such as a cooling charge coupled device (CCD) image sensor or a complementary metal-oxide semiconductor (CMOS) image sensor, and detects light reflected by the object S, fluorescence or chemiluminescence emitted from the object S, and light transmitted through the object S to generate an image signal. The image signal generated in the imaging unit 20 is subjected to, for example, amplification processing and is then output to the imaging control device 100.

The lens unit 22 is attached to the imaging unit 20. The lens unit 22 includes, for example, a plurality of lenses, and the lenses are provided movably in an arrow Z direction in order to focus on the object S. The lens unit 22 includes, for example, optical elements, such as a diaphragm and an excitation light cut filter, and adjusts the amount or wavelength of light to be detected.

The epi-illumination light source unit 24 and the transmission light source unit 26 respectively have, for example, an excitation light source and a white light source for fluorescence imaging, and the light sources are switched under the control of the imaging control device 100 as necessary. For example, when performing imaging to detect fluorescence emitted from the fluorescence-labeled object S, the object S is irradiated with excitation light from the epi-illumination light source unit 24 or the transmission light source unit 26, when performing imaging to detect reflected light from the object S, the object S is irradiated with white light from the epi-illumination light source unit 24, and when performing imaging to detect transmitted light transmitted through the object S, the object S is irradiated with white light from the transmission light source unit 26.

The object observation monitor 50 displays a state on the stage 16 which is imaged by a small camera (not shown) provided in the upper portion of the housing 12. With this, it is possible to confirm the position of the object S placed on the stage 16 or the height of the stage 16, and to adjust the position of the object or the height of the stage such that the object S is placed suitably for imaging.

The imaging device body 10 of this embodiment has the configuration described above, and can perform imaging by four imaging methods according to the type of object or the purpose of imaging. The four imaging methods include an imaging method (hereinafter, referred to as a first imaging method) which detects chemiluminescence emitted from the object, an imaging method (hereinafter, referred to as a second imaging method) which detects fluorescence emitted from the object, an imaging method (hereinafter, referred to as a third imaging method) which detects reflected light reflected by the object, and an imaging method (hereinafter, referred to as a fourth imaging method) which detects transmitted light transmitted through the object.

In the first imaging method, when an object molecule excited by a chemical reaction returns to a ground state, a phenomenon (chemiluminescence) of energy being discharged as light is used. With this, for example, genetic analysis, inspection and research of a biological tissue relating to diseases and aging, deterioration evaluation of organic compounds and polymer compounds, and the like can be performed. For example, a substance to be imaged in the object is labeled with a labeling substance which generates chemiluminescence if coming into contact with a chemiluminescent substrate, and thereafter, the chemiluminescent substrate is brought into contact with the labeling substance, whereby chemiluminescence can be generated. In the first imaging method, light irradiation from the epi-illumination light source unit 24 and the transmission light source unit 26 is not performed.

In the second imaging method, excitation light from the epi-illumination light source unit 24 or the transmission light source unit 26 is irradiated, and fluorescence from a fluorescent substance labeling a substance to be imaged in the object is detected. As an object for the second imaging method, for example, a gel support including a DNA (deoxyribonucleic acid) segment fluorescence-labeled and separated by electrophoresis is given. If the imaging device 1 of this embodiment is used, the distribution of the DNA segment in the gel support can be imaged and analyzed.

In the third imaging method, for example, white light is irradiated from the epi-illumination light source unit 24 as illumination light, and reflected light of illumination light by the object is detected. With this, a digital image can be obtained by photoelectrically reading a reflective original, such as a photograph. In the fourth imaging method, for example, white light is irradiated from the transmission light source unit 26 as illumination light, and transmitted light of illumination light transmitted through the object is detected. With this, a digital image can be obtained by photoelectrically reading a transmissive original, such as a film.

The imaging control device 100 is constituted of, for example, a personal computer, and includes a control device body 102, an input unit 104, and a display unit 106.

The imaging control device 100 controls the operations of the imaging unit 20, the epi-illumination light source unit 24, and the transmission light source unit 26 of the imaging device body 10 to control the imaging function of the object S described above. The imaging control device 100 has an analysis function of analyzing an image captured by the imaging unit 20 and a file operation function of a file including an image captured by the imaging unit 20. The analysis function and the file operation function will be described below in detail.

As shown in FIG. 4, the control device body 102 includes an image processing unit 108, an image analysis unit 110, a file operation unit 112, a terminal recognition unit 114, and a control unit 116.

The image processing unit 108 receives an image signal output from the imaging unit 20 as input, and subjects the image signal to, for example, signal processing, such as noise elimination processing or sharpness processing.

The image analysis unit 110 executes the analysis function described above, and analyzes an image of chemiluminescence captured by the first imaging method or an image of fluorescence captured by the second imaging method.

Specifically, the image analysis unit 110 acquires, for example, an image obtained by imaging chemiluminescence or fluorescence of DNA separated by electrophoresis, RNA (ribonucleic acid), or protein, acquires feature quantities, such as the position of a band in the image, the concentration of the band, and the size of the band, and analyzes the feature quantities. In the case of protein, the molecular weight of protein can be determined by the position of the band, and the expression amount of protein can be determined by the concentration and size of the band. A method of image analysis is not limited thereto, and other known methods can be used.

The file operation unit 112 executes the file operation function described above, stores a file including an image captured by the imaging unit 20, and performs a file operation of the stored file.

Information of the file stored in the file operation unit 112 is output to the first to sixth terminal devices 2 to 7 shown in FIG. 1, and the first to sixth terminal devices 2 to 7 display the input information of the file. The first to sixth terminal devices 2 to 7 receive an instruction input of a file operation from the user, and each file stored in the file operation unit 112 is subjected to a file operation based on control information output from the first to sixth terminal devices 2 to 7. Examples of the file operation include file copy, move, delete, rename, and the like. Hereinafter, the file operation will be described in detail.

The file operation is executed when a "FILE OPERATION" key K3 described below is depressed by the user in the first to sixth terminal devices 2 to 7. If the file operation function is executed, the control unit 116 of the imaging device 1 acquires information of a file name stored in the file operation unit 112, and outputs information of the file name to the first to sixth terminal devices 2 to 7.

Figure 5:
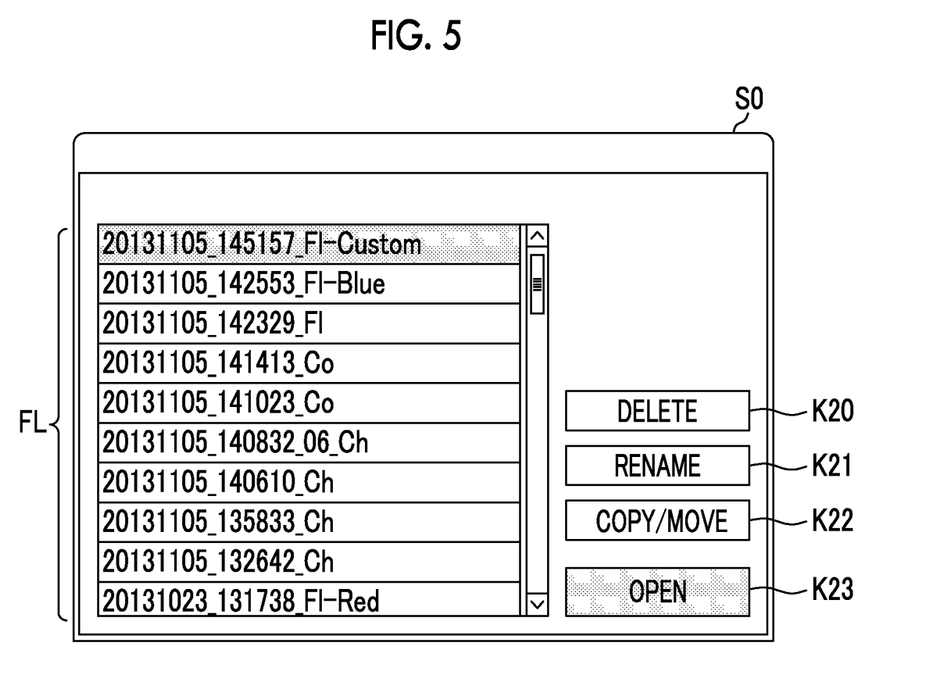
FIG. 5 is a diagram showing an example of a file operation screen.

The first to sixth terminal devices 2 to 7 receive information of the file name output from the imaging device 1 and display a file operation screen S0 shown in FIG. 5 based on the received information of the file name. In this embodiment, the file operation screen S0 is displayed on a touch panel 201 (see FIG. 6) of each of the terminal devices 2 to 7 described below.

As shown in FIG. 5, on the file operation screen S0, a file name display column FL in which file names are listed and displayed, a "DELETE" key K20 which receives an input of an instruction to delete a file, a "RENAME" key K21 which receives an input of an instruction to change a file name, a "COPY/MOVE" key K22 which receives an input of an instruction to move and copy a file, and an "OPEN" key K23 which receives an input of an instruction to open a file are displayed.

For example, in the file name display column FL, a predetermined file name is selected by the user, and a file operation is performed for the selected file. For example, when the "DELETE" key K20 is depressed by the user, the selected file name and deletion information are output from the first to sixth terminal devices 2 to 7 to the imaging device 1. The file operation unit 112 of the imaging device 1 deletes the selected file according to the input information.

When the "RENAME" key K21 is depressed by the user, an input screen of a new file name is displayed on the touch panel 201 of each of the first to sixth terminal devices 2 to 7, and an input of the new file name by the user is received. The new file name input on the input screen is output from the second to sixth terminal devices 2 to 7 to the imaging device 1. The file operation unit 112 of the imaging device 1 changes the file name of the selected file based on the input new file name.

When the "COPY/MOVE" key K22 is depressed by the user, a movement destination designation screen on which a movement destination of a copied file is designated is displayed on the touch panel 201 of each of the first to sixth terminal devices 2 to 7, and the designation of the movement destination by the user is received. The movement destination of the copied file is, for example, a predetermined drive or folder in the first to sixth terminal devices 2 to 7, a predetermined drive or folder in the network server 8 and the storage device 9 connected to the imaging device 1, or the like.

If the movement destination of the copied file is designated on the movement destination designation screen by the user, the selected file name and information of the movement destination are output from the first to sixth terminal devices 2 to 7 to the imaging device 1. The file operation unit 112 of the imaging device 1 reads the selected file to create a copy and transfers the copied file to the designated movement destination according to the input information.

When the "OPEN" key K23 is depressed by the user, the selected file name is output from the first to sixth terminal devices 2 to 7 to the imaging device 1. The file operation unit 112 of the imaging device 1 reads the selected file to create a copy and transfers the copied file to the first to sixth terminal devices 2 to 7 according to the input information. Then, the first to sixth terminal devices 2 to 7 open the transferred file and display an image on the touch panel 201. When a file which has already been transferred to the first to sixth terminal devices 2 to 7 is selected, the transfer described above is not performed, and the selected file is opened.

The terminal recognition unit 114 recognizes the first to sixth terminal devices 2 to 7 shown in FIG. 1 individually. Specifically, the terminal recognition unit 114 has a wireless communication function, acquires identification information of each terminal device output from each of the terminal devices 2 to 7 through wireless communication, and recognizes the first to sixth terminal devices 2 to 7 individually based on the identification information. As the identification information, a media access control address (MAC address) may be used. Each terminal device may be recognized using a dedicated password or the like. The terminal recognition unit 114 receives control information output from the first to sixth terminal devices 2 to 7 through wireless communication and outputs the control information to the control unit 116.

The control unit 116 includes, for example, a central processing unit (CPU), a read only memory (ROM), and the like. The control unit 116 integrally controls the operations of the imaging device body 10 and the imaging control device 100.

In particular, the control unit 116 of this embodiment receives the control information output from the first to sixth terminal devices 2 to 7, and controls the imaging function of the imaging device body 10 and the image analysis function and the file operation function of the imaging control device 100 based on the received control information.

The control unit 116 includes an authorization unit 117. The authorization unit 117 gives each of the terminal devices 2 to 7 an authority to specify a function controllable by each of the terminal devices 2 to 7. The function controllable by each of the terminal devices 2 to 7 is limited within the range of the authority given by the authorization unit 117. The function controllable by each authority will be described below in detail.

The control unit 116 of this embodiment recognizes the execution states of the above-described imaging function, the analysis function, and the file operation function by each terminal device in real time based on recognition information of each terminal device recognized by the terminal recognition unit 114 and the received control information, and displays the recognition result on the touch panel 201 of each of the terminal devices 2 to 7.

The display unit 106 includes, for example, a display device, such as a cathode ray tube (CRT) display or a liquid crystal display, and displays an image captured by the imaging unit 20, or the like. Similarly to the first to sixth terminal devices 2 to 7, the display unit 106 displays file information stored in the file operation unit 112.

The input unit 104 includes input devices, such as a mouse and a keyboard. The user performs various settings of the respective units of the imaging device body 10 and the imaging control device 100 using the input unit 104.

Next, the first to sixth terminal devices 2 to 7 will be described in detail. The first to sixth terminal devices 2 to 7 are constituted of, for example, tablet terminals. The first to sixth terminal devices 2 to 7 receive an operation instruction input of the imaging device 1 from the user and output the control information to the imaging device 1 based on the received operation instruction input.

Figure 6:
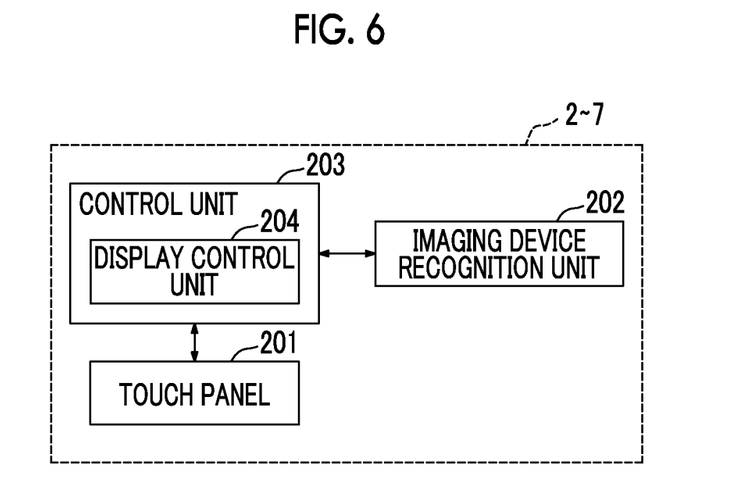
FIG. 6 is a block diagram showing the schematic configuration of first to sixth terminal devices.

FIG. 6 is a block diagram showing the schematic configuration of the first to sixth terminal devices 2 to 7. As shown in FIG. 6, the first to sixth terminal devices 2 to 7 include the touch panel 201, an imaging device recognition unit 202, and a control unit 203.

The touch panel 201 displays an operation instruction input screen on which an operation instruction input of the imaging device 1 from the user is received, and receives an instruction input of the above-described imaging function, the analysis function, and the file operation function on the operation instruction input screen. The operation instruction input screen will be described below in detail.

The imaging device recognition unit 202 recognizes the imaging device 1 and outputs control information according to the operation instruction input from the user to the imaging device 1. Specifically, the imaging device recognition unit 202 has a wireless communication function, recognizes the imaging device 1 through wireless communication, and outputs the control information. The imaging device recognition unit 202 acquires information of the execution state of the imaging function, the analysis function, and the file operation function in the imaging device 1.

The control unit 203 integrally controls the operation of the terminal device. The control unit 203 outputs the control information according to the operation instruction input from the user to the imaging device recognition unit 202.

The control unit 203 includes a display control unit 204, and the display control unit 204 displays the operation instruction input screen described above on the touch panel 201. The display control unit 204 displays the execution state of the function in each of the terminal devices 2 to 7 in the imaging device 1 acquired by the imaging device recognition unit 202 on the touch panel 201 in real time. The display control by the display control unit 204 will be described below in detail.

In this embodiment, although tablet terminals are used as the first to sixth terminal devices 2 to 7, the invention is not limited thereto, and a personal computer connected through a wireless communication line or a wired communication line, such as a local area network (LAN), may be used.

The network server 8 is a data server which is designated as a movement destination of a file stored in the file operation unit 112 of the imaging device 1, and is connected to the imaging device 1 through a wireless communication line or a wired communication line. The storage device 9 is also a storage medium which is designated as a movement destination of a file stored in the file operation unit 112 of the imaging device 1, and is constituted of, for example, a universal serial bus (USB) memory, a USB hard disk, or the like.

Next, the action of the imaging system of this embodiment will be described referring to the drawings. The imaging system of this embodiment has a feature in that each of the terminal devices 2 to 7 is authorized by the authorization unit 117, and description will be provided focusing on this feature.

Figure 7:
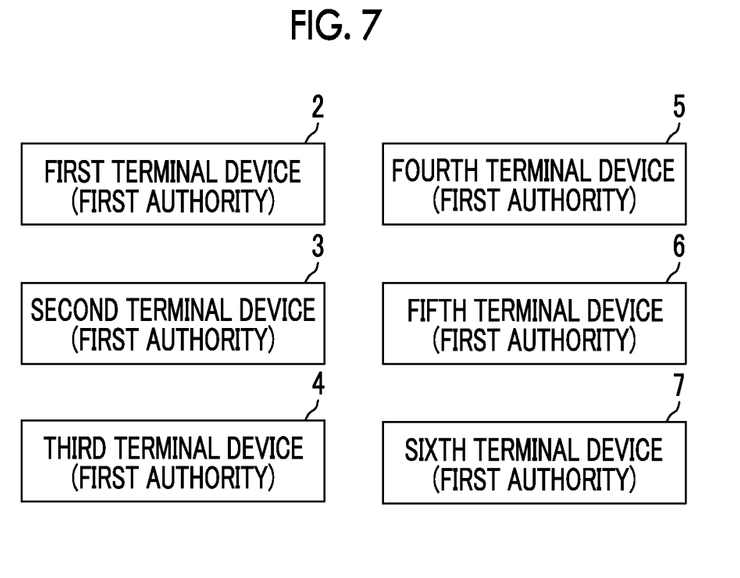
FIG. 7 is a diagram showing a state where the first to sixth terminal devices are given a first authority when the imaging device is not controlled by the terminal devices.

First, in a state where all terminal devices do not control the imaging device 1, as shown in FIG. 7, the first to sixth terminal devices 2 to 7 are given a first authority. The state of the authorization in each of the terminal devices 2 to 7 shown in FIG. 7 is hereinafter referred to as a first state.

Figure 8:
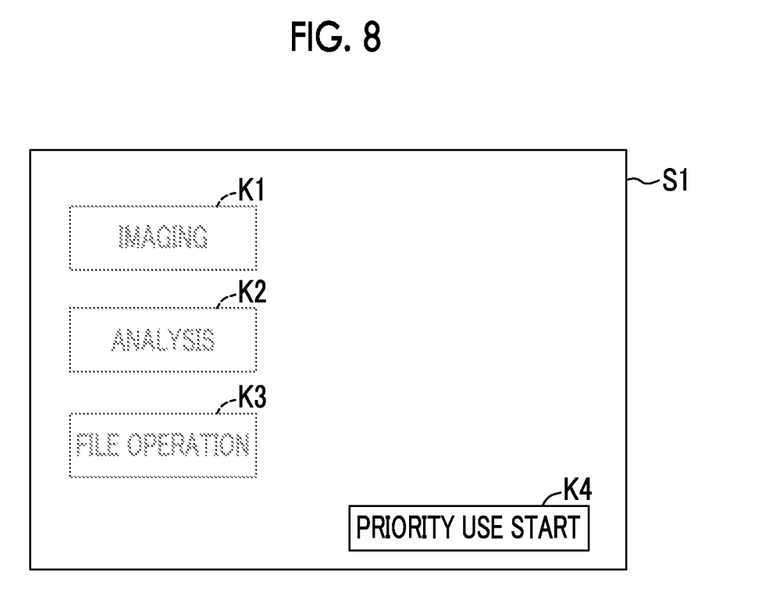
FIG. 8 is a diagram showing an example of an operation instruction input screen which is displayed on the first to sixth terminal devices given the first authority.

Here, the first authority is an authority capable of allowing the first to sixth terminal devices 2 to 7 to exclusively occupy the imaging function of the imaging device 1 and to bring the imaging function into a controllable state. Specifically, an operation instruction input screen S1 shown in FIG. 8 is displayed on the touch panel 201 of each of the first to sixth terminal devices 2 to 7. An "IMAGING" key K1 which receives an instruction to execute the imaging function, an "ANALYSIS" key K2 which receives an instruction to execute the analysis function, a "FILE OPERATION" key K3 which receives an instruction to execute the file operation, and a "PRIORITY USE START" key K4 which receives an input of a priority use of the imaging function are displayed on the operation instruction input screen S1.

However, in the first state, the "IMAGING" key K1, the "ANALYSIS" key K2, and the "FILE OPERATION" key K3 are grayed out, and the reception of the operation instruction inputs using these keys is disabled.

In one terminal device of the first to sixth terminal devices 2 to 7, if the "PRIORITY USE START" key K4 is depressed by the user (corresponding to a first instruction operation of the invention), the "IMAGING" key K1, the "ANALYSIS" key K2, and the "FILE OPERATION" key K3 of the terminal device are active-displayed, the operation instruction inputs of these functions are enabled, and next, if the "IMAGING" key K1 is depressed by the user, the imaging function of the imaging device 1 is held by the terminal device.

For example, if the "PRIORITY USE START" key K4 and the "IMAGING" key K1 are depressed in the first terminal device 2, the control unit 203 of the first terminal device 2 generates control information for controlling the imaging function. Then, the control information for controlling the imaging function and the identification information of the first terminal device 2 are output from the imaging device recognition unit 202 of the first terminal device 2 to the imaging device 1.

The imaging device 1 executes the imaging function if the control information of the imaging function output from the first terminal device 2 is received.

Figure 9:
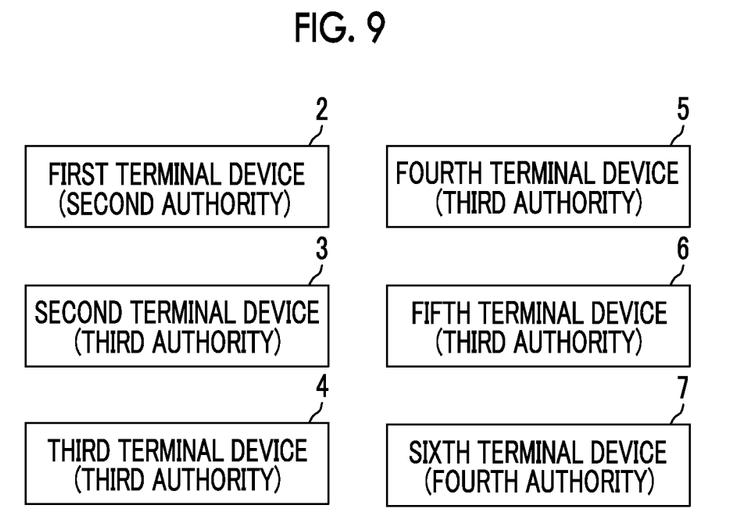
FIG. 9 is a diagram showing a state where the first terminal device is given a second authority, the second to fifth terminal devices are given a third authority, and the sixth terminal device is given a fourth authority.

During the execution of the imaging function in the first terminal device 2, as shown in FIG. 9, the first terminal device 2 is given a second authority, the second to fifth terminal devices 3 to 6 are given a third authority, and the sixth terminal device 7 is given a fourth authority. The state of the authorization in each of the terminal devices 2 to 7 shown in FIG. 9 is hereinafter referred to as a second state.

Figure 10:
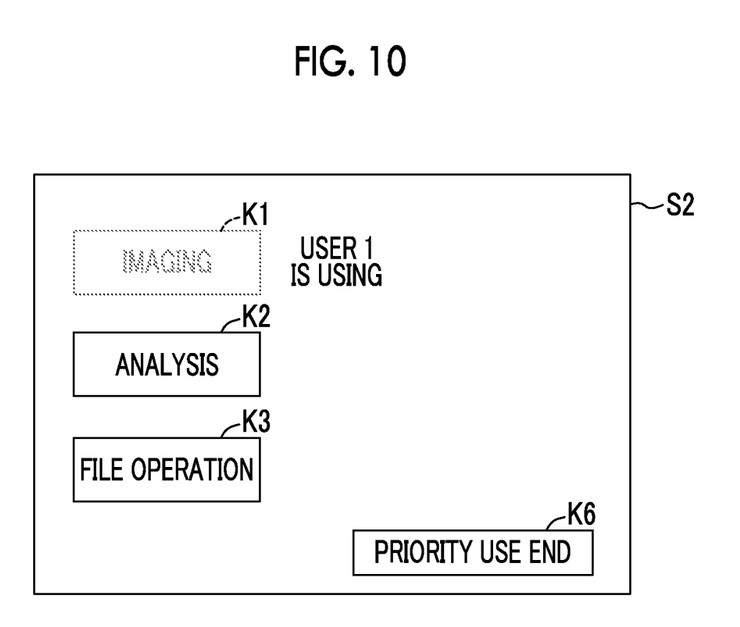
FIG. 10 is a diagram showing an example of an operation instruction input screen which is displayed on the first terminal device given the second authority.

Here, the second authority is an authority capable of exclusively occupying and controlling the imaging function as described above and releasing the occupation. Specifically, an operation instruction input screen S2 shown in FIG. 10 is displayed on the touch panel 201 of the first terminal device 2 given the second authority. On the operation instruction input screen S2, the "IMAGING" key K1 which is being already executed is grayed out, the "ANALYSIS" key K2 and the "FILE OPERATION" key K3 are active-displayed, and the reception of the operation instruction inputs of these keys is enabled.

The "PRIORITY USE START" key K4 is changed to a "PRIORITY USE END" key K6. If the "PRIORITY USE END" key K6 is depressed by the user (corresponding to a second instruction operation of the invention), the occupation of the imaging function in the first terminal device 2 is released. On the right side of the "IMAGING" key K1, a message of "USER 1 IS USING" indicating that a first user executes the imaging function of the imaging device 1 using the first terminal device 2 is displayed. This message is displayed based on information of the execution state of the function of the imaging device 1 output from the control unit 116 of the imaging device 1.

Figure 11:
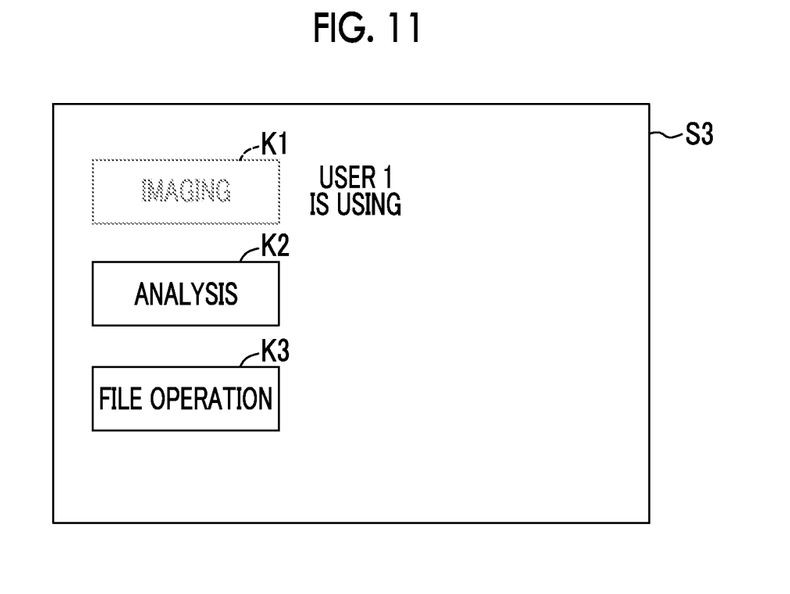
FIG. 11 is a diagram showing an example of an operation instruction input screen which is displayed on the second to fifth terminal devices given the third authority.

The third authority given to the second to fifth terminal devices 3 to 6 is an authority with the restriction of the control of the imaging function held by the first terminal device 2. Specifically, an operation instruction input screen S3 shown in FIG. 11 is displayed on the touch panel 201 of each of the second to fifth terminal devices 3 to 6 given the third authority. On the operation instruction input screen S3, the "IMAGING" key K1 which is being already executed by the first terminal device 2 is grayed out, the "ANALYSIS" key K2 and the "FILE OPERATION" key K3 are active-displayed, and the reception of the operation instruction inputs of these keys is enabled. Similarly to the first terminal device 2, on the right side of the "IMAGING" key K1, a message of "USER 1 IS USING" indicating that the first user executes the imaging function of the imaging device 1 using the first terminal device 2 is displayed. That is, the second to fifth terminal devices 3 to 6 given the third authority cannot execute the imaging function which is being executed by the first terminal device 2, but can execute the analysis function and the file operation function. In the second to fifth terminal devices 3 to 6, when the "ANALYSIS" key K2 or the "FILE OPERATION" key K3 is depressed by the user, the imaging function in the first terminal device 2 and the analysis function or the file operation function in the second to fifth terminal devices 3 to 6 are executed in parallel.

However, in the second to fifth terminal devices 3 to 6 given the third authority, the "PRIORITY USE START" key K4 is not changed to the "PRIORITY USE END" key K6, and is non-displayed. That is, the second to fifth terminal devices 3 to 6 cannot release the occupation of the imaging function in the first terminal device 2, and cannot receive the operation instruction input of "PRIORITY USE START".

The fourth authority given to the sixth terminal device 7 is an authority capable of releasing the occupation state of the imaging function in the first terminal device 2 given the second authority, in addition to the third authority described above. In this way, the sixth terminal device 7 given the fourth authority is given an authority capable of releasing the occupation state of the imaging function in the first terminal device 2 other than the sixth terminal device 7, and this is because a case where, for example, in a state where the imaging function is held by the first terminal device 2, the user of the terminal device forgets to release the occupation is considered. In such a case, since the occupation state of the imaging function in the first terminal device 2 is continued and the imaging function is unusable by other users, a specific terminal device among a plurality of terminal devices connected to the imaging device 1 is given the fourth authority described above, and the occupation state is forcibly releasable by the specific terminal device.

Figure 12:
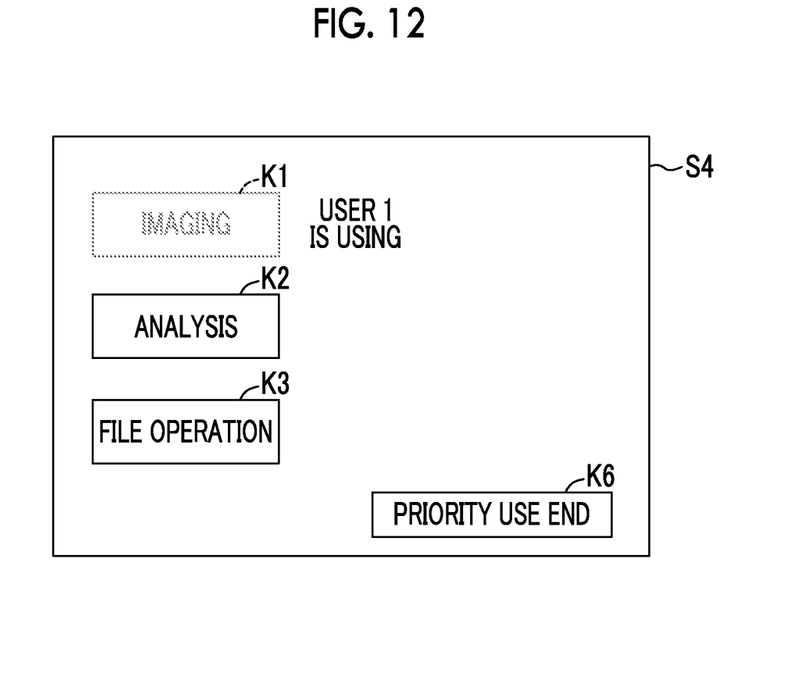
FIG. 12 is a diagram showing an example of an operation instruction input screen which is displayed on the sixth terminal device given the fourth authority.

Specifically, an operation instruction input screen S4 shown in FIG. 12 is displayed on the touch panel 201 of the sixth terminal device 7 given the fourth authority. On the operation instruction input screen S4, similarly to the second to fifth terminal devices 2 to 6, the "IMAGING" key K1 which is being already executed by the first terminal device is grayed out, the "ANALYSIS" key K2 and the "FILE OPERATION" key K3 are active-displayed, and the reception of the operation instruction inputs of these keys is enabled. Similarly to the first terminal device 2, on the right side of the "IMAGING" key K1, a message of "USER 1 IS USING" indicating that the first user executes the imaging function of the imaging device 1 using the first terminal device 2 is displayed. That is, the sixth terminal device 7 given the fourth authority cannot execute the imaging function which is being executed by the first terminal device 2, but can execute the analysis function and the file operation function. In the sixth terminal device 7, when the "ANALYSIS" key K2 or the "FILE OPERATION" key K3 is depressed by the user, the imaging function in the first terminal device 2 and the analysis function or the file operation function in the sixth terminal device 7 are executed in parallel.

In the sixth terminal device 7 given the fourth authority, similarly to the first terminal device 2, the "PRIORITY USE START" key K4 is changed to the "PRIORITY USE END" key K6. If the "PRIORITY USE END" key K6 is depressed by the user, the occupation of the imaging function in the first terminal device 2 is released.

In the second state described above, when the "PRIORITY USE END" key K6 is depressed by the user in the first terminal device 2 or the "PRIORITY USE END" key K6 is depressed by the user in the sixth terminal device 7 (corresponding to a third instruction operation of the invention), the second state is switched to the first state described above. That is, as shown in FIG. 7, the second state is switched to a state where the first to sixth terminal devices 2 to 7 are given the first authority, and the occupation of the imaging function in one terminal device among the first to sixth terminal devices 2 to 7 is enabled.

According to the imaging system of the embodiment described above, as described above, since an authority which is given to each terminal device is switched from the first state to the second state, the user of the terminal device given the second authority can execute the imaging function at an appropriate timing without being affected or obstructed by other terminal devices.

In the terminal device given the second authority, when the occupation state of the imaging function is released, an authority which is given to each terminal device can be returned from the second state to the first state, the users of other terminal devices can exclusively occupy the imaging function and can bring the imaging function into a controllable state quickly, and as a result, the use efficiency of the imaging device can be improved.

Since the execution state of the imaging function of other terminal devices is displayed in each of the terminal devices 2 to 7, even at a place where the user of each of the terminal devices 2 to 7 is separated from the imaging device 1, the execution state of the imaging function can be understood immediately, and as a result, the start of the priority use of the imaging function can be performed quickly. Therefore, the use efficiency of the imaging device can be improved.

In the above description, although a case where the first terminal device 2 exclusively occupies the imaging function has been described, the second to sixth terminal devices 3 to 7 may receive the input of the "PRIORITY USE START" key K4 to exclusively occupy the imaging function.

Figure 13:
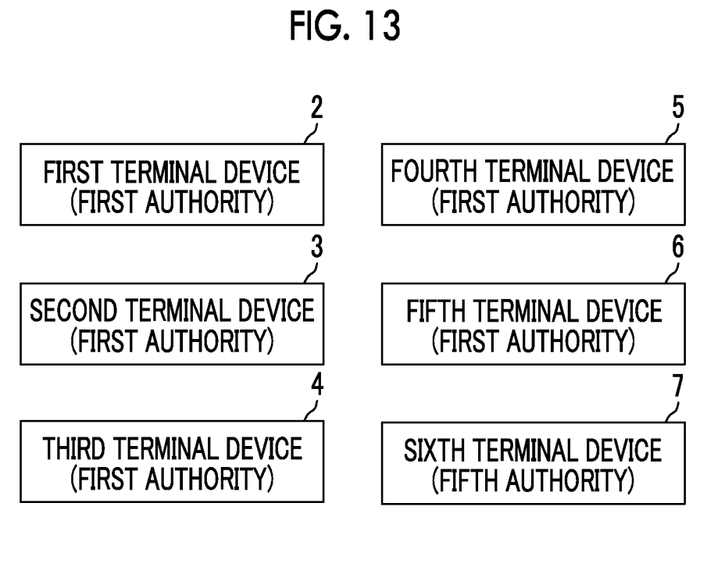
FIG. 13 is a diagram showing a state where the first to fifth terminal devices are given the first authority and the sixth terminal device is given a fifth authority.

In the embodiment described above, although the sixth terminal device 7 is given the first authority in the first state and is given the fourth authority in the second state, as shown in FIG. 13, a fifth authority may be given in the first state.

The fifth authority is an authority which includes an authority to give the first to fifth terminal devices 2 to 6 given the first authority a sixth authority to prohibit the use of the imaging device 1, in addition to the first authority.

Figure 14:
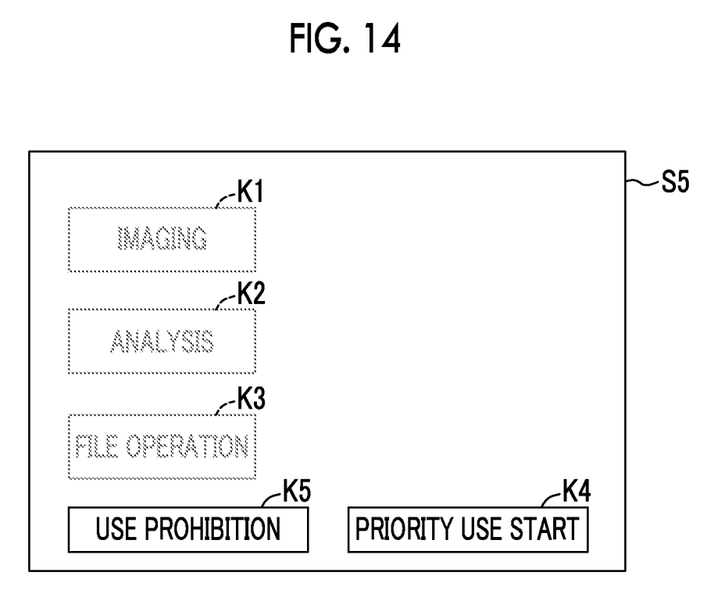
FIG. 14 is a diagram showing an example of an operation instruction input screen which is displayed on the sixth terminal device given the fifth authority.

Specifically, an operation instruction input screen S5 shown in FIG. 14 is displayed on the touch panel 201 of the sixth terminal device 7 given the fifth authority. On the operation instruction input screen S5, similarly to the first to fifth terminal devices 2 to 6 in the first state, the "IMAGING" key K1, the "ANALYSIS" key K2, and the "FILE OPERATION" key K3 are grayed out. Then, the "PRIORITY USE START" key K4 and a "USE PROHIBITION" key K5 are displayed.

Figure 15:
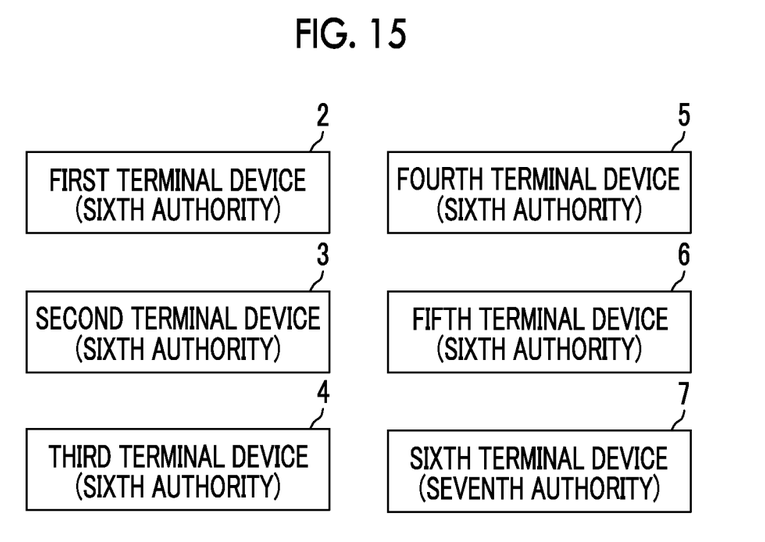
FIG. 15 is a diagram showing a state where the first to fifth terminal devices are given a sixth authority and the sixth terminal device is given the seventh authority.

If the "USE PROHIBITION" key K5 is depressed by the user (corresponding to a fourth instruction operation of the invention), as shown in FIG. 15, the first to fifth terminal devices 2 to 6 are given the sixth authority to prohibit the use of the imaging device 1, and the sixth terminal device 7 is given a seventh authority including an authority to release the use prohibition of the imaging device 1 by the first to fifth terminal devices 2 to 6. The state of the authorization in each of the terminal devices 2 to 7 shown in FIG. 15 is hereinafter referred to as a third state.

Figure 16:
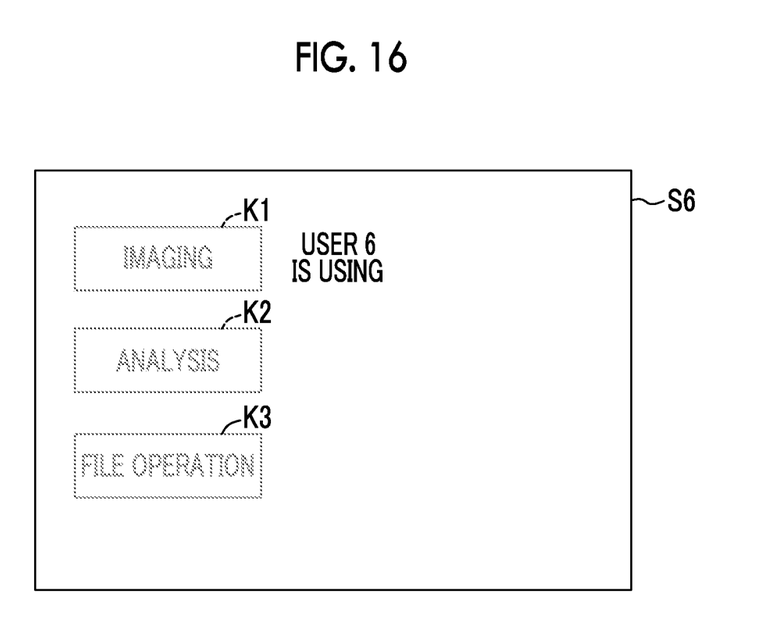
FIG. 16 is a diagram showing an example of an operation instruction input screen which is displayed on the first to fifth terminal devices given the sixth authority.

Specifically, an operation instruction input screen S6 shown in FIG. 16 is displayed on the touch panel 201 of each of the first to fifth terminal devices 2 to 6 given the sixth authority. On the operation instruction input screen S6, the "IMAGING" key K1, the "ANALYSIS" key K2, and the "FILE OPERATION" key K3 are grayed out, and the "PRIORITY USE START" key K4 is not displayed. However, on the operation instruction input screen S6, information of the execution state of the imaging function of the sixth terminal device 7 is displayed. That is, for example, when the imaging function of the imaging device 1 is executed by the sixth terminal device 7, on the right side of the "IMAGING" key K1, a message of "USER 6 IS USING" indicating that a sixth user executes the imaging function of the imaging device 1 using the sixth terminal device 7 is displayed.

Figure 17:
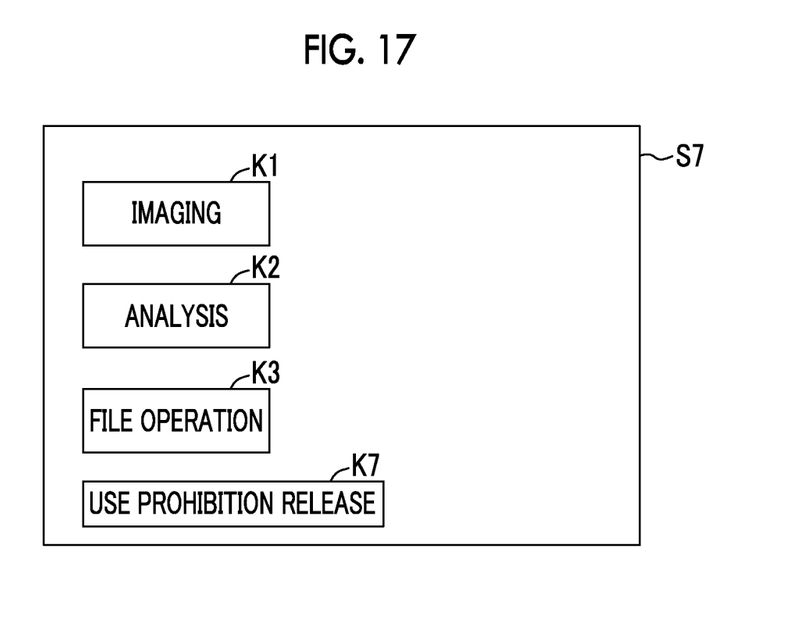
FIG. 17 is a diagram showing an example of an operation instruction input screen which is displayed on the sixth terminal device given a seventh authority.

An operation instruction input screen S7 shown in FIG. 17 is displayed on the touch panel 201 of the sixth terminal device 7 given the seventh authority. On the operation instruction input screen S7, the "IMAGING" key K1, the "ANALYSIS" key K2, and the "FILE OPERATION" key K3 become active, and the operation instruction inputs of these keys are enabled. The "USE PROHIBITION" key K5 is changed to a "USE PROHIBITION RELEASE" key K7, and the "PRIORITY USE START" key K4 is non-displayed.

If the "USE PROHIBITION RELEASE" key K7 is depressed by the user in the sixth terminal device 7 (corresponding to a fifth instruction operation of the invention), the use prohibition of the imaging device 1 by the first to fifth terminal devices 2 to 6 is released, and an authority given to the first to sixth terminal devices 2 to 7 is switched to the first state described above.

Figure 18:
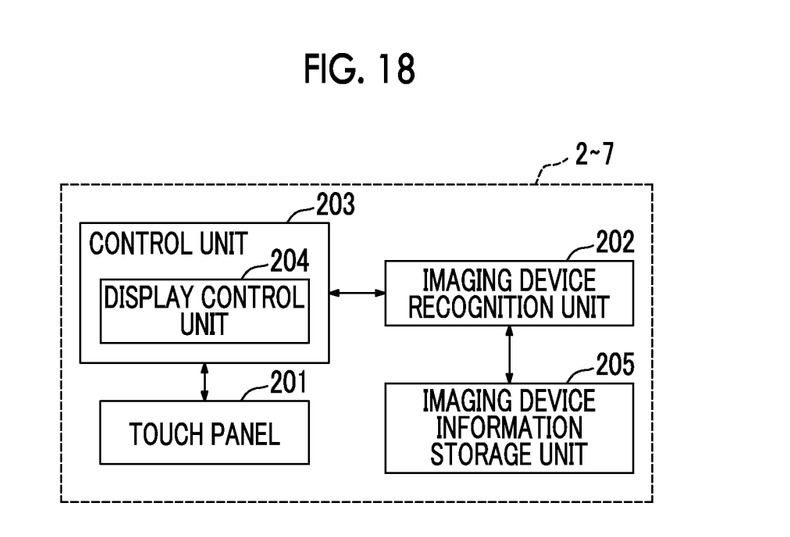
FIG. 18 is a block diagram showing another embodiment of a terminal device.

In the description of the embodiment described above, although a case where the functions of one imaging device 1 are controlled by a plurality of terminal devices has been described, the number of imaging devices 1 may not necessarily be one, and the functions of a plurality of imaging devices may be controlled by a plurality of terminal devices. In this case, for example, as shown in FIG. 18, an imaging device information storage unit 205 which stores registration information of a plurality of imaging devices may be provided in each terminal device, and an imaging device recognition unit 202 may recognize a plurality of imaging devices based on the registration information. The control of the functions of each imaging device by a plurality of terminal devices is the same as in the embodiment described above.

Figure 19:
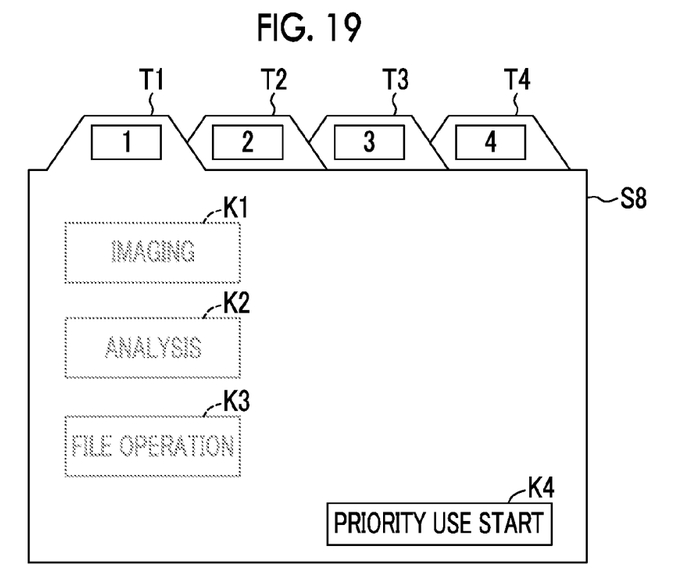
FIG. 19 is a diagram showing an example of an operation instruction input screen which is displayed on terminal devices when there are a plurality of imaging devices.

FIG. 19 shows an example of an operation instruction input screen S8 which is displayed on each terminal device when there are a plurality of imaging devices. The operation instruction input screen S8 shown in FIG. 19 is an example when there are four imaging devices, and four tags T1 to T4 for receiving operation instruction inputs of respective functions of respective imaging devices are displayed.

FIG. 19 shows an operation instruction input screen when the tag T1 is selected, and on the operation instruction input screen, an operation instruction input of each function of a first imaging device is received. FIG. 19 shows an operation instruction input screen when an authority given to each terminal device by the first imaging device is the first state described above. When the tag T2 is selected, the operation instruction input screen is changed, and an operation instruction input of each function of a second imaging device is received. In this way, the user can select an imaging device to be controlled by selecting the tags T1 to T4.

Figure 20:
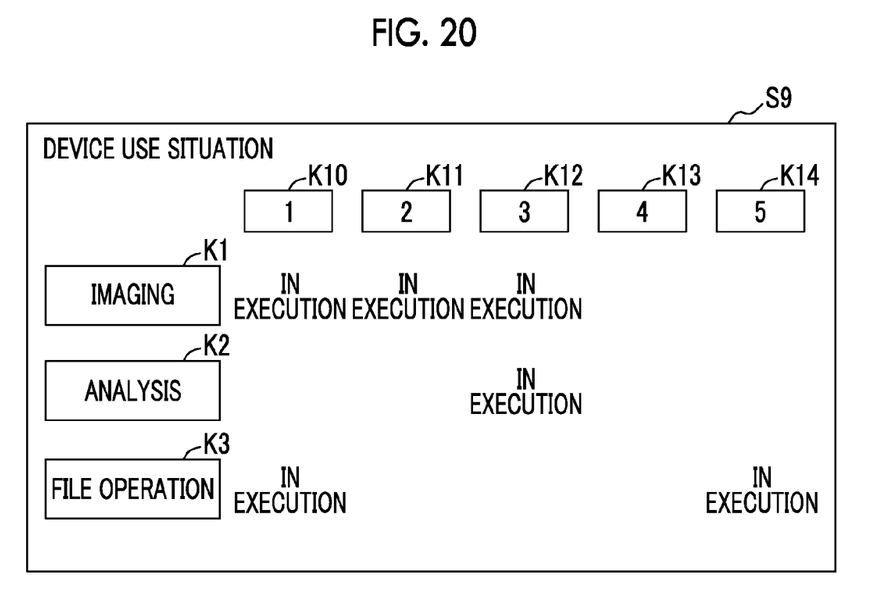
FIG. 20 is a diagram showing an example of list display of imaging devices displayed on terminal devices when there are a plurality of imaging devices.

When there are a plurality of imaging devices, execution information of each function in each imaging device may be listed and displayed in each imaging device. FIG. 20 shows an example of a list display screen S9 when there are five imaging devices. On the list display screen S9, imaging device selection keys K10 to K14 are displayed, and execution information of each function of each imaging device is displayed below each key. For example, execution information indicating that an imaging function and a file operation function in a first imaging device are being executed is displayed below the imaging device selection key K10, and execution information indicating that only an imaging function in a second imaging device is being executed is displayed below the below imaging device selection key K11. For example, when each of the imaging device selection keys K10 to K14 is depressed by the user, an operation instruction input screen of an imaging device corresponding to the imaging device selection key is displayed, execution information of the imaging device is displayed, and an operation instruction input from the user is enabled. As a plurality of imaging devices, imaging devices of different types may be used.

What is claimed is:
1. An imaging system comprising:
   an imaging device which photoelectrically reads fluorescence or chemiluminescence emitted from an object to image the object;
   a plurality of terminal devices which output control information for controlling the imaging device to the imaging device; and an authorization unit which gives the respective terminal devices an authority to specify controllable functions of the imaging device, wherein the authorization unit switches between a first state where the respective terminal devices are given a first authority to exclusively occupy a part of functions of the imaging device and to bring the part of functions into a controllable state; and a second state where one terminal device among the plurality of terminal devices is given a second authority to exclusively occupy and control the part of functions and to release the occupation, and the terminal devices other than one terminal device are given a third authority with the restriction of the control of the part of functions.

2. The imaging system according to claim 1, wherein the first authority includes an authority capable of receiving a first instruction operation to exclusively occupy a part of functions of the imaging device and to bring the part of functions into a controllable state, and the authorization unit switches from the first state to the second state when receiving the first instruction operation.

3. The imaging system according to claim 2, wherein the third authority does not include an authority capable of receiving the first instruction operation.

4. The imaging system according to claim 1, wherein the second authority includes an authority capable of receiving a second instruction operation to release the occupation of the part of functions, and the authorization unit switches from the second state to the first state when receiving the second instruction operation.

5. The imaging system according to claim 2, wherein the second authority includes an authority capable of receiving a second instruction operation to release the occupation of the part of functions, and the authorization unit switches from the second state to the first state when receiving the second instruction operation.

6. The imaging system according to claim 3, wherein the second authority includes an authority capable of receiving a second instruction operation to release the occupation of the part of functions, and the authorization unit switches from the second state to the first state when receiving the second instruction operation.

7. The imaging system according to claim 1,
wherein the part of functions is a function of imaging.

8. The imaging system according to claim 2,
wherein the part of functions is a function of imaging.

9. The imaging system according to claim 3,
wherein the part of functions is a function of imaging.

10. The imaging system according to claim 4,
wherein the part of functions is a function of imaging.

11. The imaging system according to claim 5,
wherein the part of functions is a function of imaging.

12. The imaging system according to claim 1, wherein the authorization unit gives a specific terminal device other than terminal devices given the second authority a fourth authority including an authority to release the occupation of the part of functions by the terminal device given the second authority in the second state.

13. The imaging system according to claim 12, wherein the fourth authority includes an authority capable of receiving a third instruction operation to release the occupation of the part of functions, and the authorization unit switches from the second state to the first state when receiving the third instruction operation.

14. The imaging system according to claim 12, wherein the authorization unit gives the specific terminal device a fifth authority in the first state, and the fifth authority includes an authority to give the terminal devices other than the specific terminal device a sixth authority with the restriction of controllable functions further than the third authority.

15. The imaging system according to claim 14, wherein the fifth authority includes an authority capable of receiving a fourth instruction operation to give the terminal devices other than the specific terminal device the sixth authority, and the authorization unit switches to a third state where the terminal devices other than the specific terminal device are given the sixth authority when receiving the fourth instruction operation in the first state.

16. The imaging system according to claim 14, wherein the authorization unit gives the specific terminal device a seventh authority in the third state, and the seventh authority includes an authority to release the restriction of the controllable functions in the terminal devices other than the specific terminal device.

17. The imaging system according to claim 14, wherein the fifth authority includes an authority capable of receiving a fifth instruction operation to release the restriction of the controllable functions in the terminal devices other than the specific terminal device, and the authorization unit gives the terminal devices other than the specific terminal device the first authority when receiving the fifth instruction operation in the third state.

18. The imaging system according to claim 14, wherein the fifth authority includes an authority to prohibit the control of the imaging device by the terminal devices other than the specific terminal device.

19. The imaging system according to claim 15, wherein the fourth instruction operation is an instruction operation to prohibit the control of the imaging device by the terminal devices other than the specific terminal device.

20. The imaging system according to claim 17, wherein the fifth instruction operation is an instruction operation to release the prohibition of the control of the imaging device by the terminal devices other than the specific terminal device.

* * * * *